United States Patent [19]

Markley

[11] 4,087,473
[45] May 2, 1978

[54] PREFERENTIAL ALIPHATIC HALOGENATION OF AR-SUBSTITUTED ALKYLBENZENES

[75] Inventor: Lowell D. Markley, Clayton, Calif.

[73] Assignee: The Dow Chemical Company, Midland, Mich.

[21] Appl. No.: 738,401

[22] Filed: Nov. 3, 1976

[51] Int. Cl.² ............................................. C07C 25/14
[52] U.S. Cl. .............................................. 260/651 R
[58] Field of Search ................................... 260/651 R

[56] References Cited

U.S. PATENT DOCUMENTS

| 2,193,823 | 3/1940 | Levine et al. | 260/650 R |
| 2,265,312 | 12/1941 | Quattlebaum et al. | 260/650 R |
| 2,432,737 | 12/1947 | Erickson et al. | 260/650 R |
| 3,190,825 | 6/1965 | Huyser | 260/651 R |
| 3,553,274 | 1/1971 | Lewis et al. | 260/650 R |

FOREIGN PATENT DOCUMENTS

| 669,800 | 9/1963 | Canada | 260/651 R |
| 2,604,276 | 5/1976 | Germany | 260/651 R |
| 4,327,212 | 11/1968 | Japan | 260/651 R |

*Primary Examiner*—O. R. Vertiz
*Assistant Examiner*—Wayne A. Langel
*Attorney, Agent, or Firm*—Michael S. Jenkins

[57] ABSTRACT

In an isomeric mixture of ar-substituted-1-(sec-alkyl)-benzenes, such as a mixture of 2,4-dichlorocumene and 3,5-dichlorocumene, the alkyl group of the 3,5-isomer reacts preferentially with a halogen in the presence of a catalyst such as benzoyl peroxide to form a 3,5-dihalo-(α-alkyl, α-halo)alkylbenzene such as 3,5-dichloro-α-bromocumene.

9 Claims, No Drawings

PREFERENTIAL ALIPHATIC HALOGENATION OF AR-SUBSTITUTED ALKYLBENZENES

BACKGROUND OF THE INVENTION

This invention relates to processes for the preparation of ar-substituted alkylbenzenes and to a process for the preferential aliphatic halogenation of one isomer in an isomeric mixture of ar-substituted alkylbenzenes.

It is known in the art that 2,4-dihalo-1-alkylbenzenes can be isomerized to 3,5-dihalo-1-alkylbenzenes in the presence of a catalyst containing aluminum and bromine. See, for example, U.S. Pat. No. 3,553,274.

It is also known in the art that aliphatic (side chain) halogenation of, among other isomers, the ar,ar-dihaloethylbenzenes can be catalyzed by phosphorus trihalide or phosphorus pentahalide. Such reactions are typically conducted in the liquid phase at a temperature of between about 40° C and about 80° C. U.S. Pat. No. 2,265,312 teaches that the above-mentioned catalysts are useful in carrying out such aliphatic halogenation reactions.

In U.S. Pat. No. 2,432,737, a method is taught for the production of a mixture of ring isomers of dichlorostyrene. Both α-chlorination and β-chlorination of the side chains of a mixture of ethyldichlorobenzene isomers result under the conditions of the process which are the bubbling of liquid chlorine through the mixture of isomers at a temperature of about 40° C to 80° C in the presence of a catalyst such as $PCl_3$.

In U.S. Pat. No. 2,193,823, a method is taught for selective α-chlorination of an ethyl side chain of an ar-halo-ar-ethylbenzene. For example, this patent describes chlorinating the α-carbon of ethylpentachlorobenzene by contacting the same in the liquid phase with chlorine gas in the presence of the light of an ordinary electric light bulb to produce α-chloroethylpentachlorobenzene.

Heretofore, the preferential aliphatic halogenation of one isomer in a mixture of ar-substituted alkylbenzenes has not been disclosed.

SUMMARY OF THE INVENTION

The present invention is a process for the preferential, aliphatic halogenation of a 3-substituted-1-(sec-alkyl)-benzene isomer present in an isomeric mixture of ring-substituted-1-(sec-alkyl)benzenes. The isomer that is preferentially halogenated has a substituent in at least the 3-ring position and optionally in the 4- and 5-ring positions (hereinafter called 3-isomer). The remaining isomer(s) which is not halogenated in the process is a 2-substituted-1-(sec-alkyl)benzene having a substituent in at least the 2-ring position and optionally in the 3- and 4-ring positions (hereinafter called 2-isomer).

The process comprises contacting the isomeric mixture with a suitable halogen in the presence of an amount of a free radical generator and under conditions sufficient to preferentially halogenate the 3-isomer in the alpha position of the 1-sec-alkyl substituent. This preferential halogenation is surprising in that it occurs only at the alpha position of essentially all of the 3-isomer(s) while essentially none of the 2-isomer(s) is halogenated. Thus, the product of the preferential, aliphatic halogenation reaction is a mixture comprising the α-halogenated 3-isomer and the 2-isomer. The halogenated products of this process are useful as intermediates in the synthesis of useful organic compounds.

Of particular interest in the practice of this invention is a process for the preferential, aliphatic halogenation of a 3-isomer which has substituents in the 3- and 5-ring positions and optionally a substituent in the 4-ring position (hereinafter called 3,5-isomer) in an isomeric mixture also containing a 2-isomer having substituents in the 2- and 4-ring positions and optionally a substituent in the 3-ring position (hereinafter called 2,4-isomer). The α-halogenated 3,5-isomer(s) of this particular process is readily separated from the unreacted 2,4-isomer(s). The α-halogenated 3,5-isomers are useful as intermediates in the manufacture of herbicides.

DETAILED DESCRIPTION OF THE EMBODIMENTS

In the practice of the present invention it is essential to employ: an isomeric mixture, a halogen, and a free radical generator. A solvent is optionally employed.

Isomeric mixtures of particular interest contain a substituted-1-(sec-alkyl)benzene of structure (I) (herein called a 2,4-isomer) and a substituted-1-(sec-alkyl) benzene of structure (II) (herein called a 3,5-isomer).

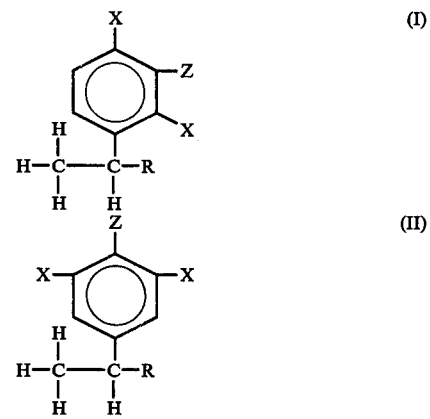

In structures (I) and (II), each X is independently methyl, chloro, bromo, fluoro, —$CF_3$ or —$CCl_3$. Preferably, each X is independently chloro, bromo or fluoro. Most preferably, each X is chloro. Z can be a group as defined for X or can be ethyl or hydrogen. Preferably, Z is hydrogen, chloro, bromo or fluoro, more preferably hydrogen or chloro. In a most preferred embodiment, Z is hydrogen. The R of structures (I) and (II) is a straight- or branched-chain alkyl group having from 1 to about 6 carbon atoms, preferably from 1 to about 3 carbon atoms. Mixtures of formulas (I) and (II) wherein each R is methyl, each Z is hydrogen, and each X is independently chloro, bromo or fluoro, constitute preferred embodiments of the present invention.

The isomeric mixtures of particular interest can be prepared in any of a number of ways. One method is isomerization of the compound of structure (I) in the presence of a catalyst containing aluminum and bromine. Such a process is taught in Example 1 of U.S. Pat. No. 3,553,274. The product of the isomerization step is a mixture containing a substantial amount of 3,5-isomer along with unreacted 2,4-isomer.

Also suitable isomeric mixtures are those containing (1) a suitable 3-isomer [e.g., 3-halo-1-(sec-alkyl)benzene, 3,4-dihalo-1-(sec-alkyl)benzene, 3-methyl-4-halo-1-(sec-alkyl)benzene and similar isomers having a substituent as defined for X hereinbefore in the 3-ring position and sec-alkyl in the 1-ring position] and (2) a suitable 2-isomer [e.g., 2-halo-1-(sec-alkyl)benzene, 2-methyl-1-(sec-alkyl)benzene and similar isomers having a substituent as defined for X hereinbefore in the 2-ring position and sec-alkyl in the 1-ring position].

The employment of a halogenating agent is the second critical aspect of the invention and halogens such as bromine and iodine are suitably employed, with bromine being the most preferred. Chlorine halogenating agents, however, are not operable in the present invention. A suitable halogen gas or any agent that is capable of generating the suitable halogen atom can be used, such as a suitable halogen-containing solid or liquid, or a compound such as N-bromo-acetamide or N-bromo-succinimide. Suitable halogens are preferably supplied at a ratio of about one mole of halogen atoms per mole of 3-isomer. While excess halogenating agent can be employed, too large an excess may lead to halogenation of the 2-isomer.

A third essential aspect for the practice of the preferential aliphatic halogenation is a free radical generator. Suitable free radical generators include ultraviolet light and/or a catalyst capable of supplying free oxygen atoms such as a peroxide. In the case of a peroxide, a quantity is used sufficient to cause halogenation of the 3-isomer (which includes the 3,5-isomer as defined hereinbefore). If a peroxide such as benzoyl peroxide is used, it is conveniently added to the isomeric mixture along with the optional solvent. With a peroxide, an amount sufficient to cause halogenation of the 3-isomer is typically between about 1 percent and about 5 percent based upon the weight of the isomeric mixture, and preferably between about 2.5 percent and about 4.0 percent based upon the weight of the isomeric mixture.

Generally, a solvent, such as benzene or carbon tetrachloride is used in the preferential, aliphatic halogenation, although the reaction can be conducted neat if desired. If used, the solvent is most advantageously employed in an amount between about 1 and about 2 g. of solvent per gram of isomeric mixture.

The preferential, aliphatic halogenation step is advantageously conducted in the liquid phase at a temperature of between about 15° C and about 65° C, and preferably between about 30° C and about 45° C. The halogenation step is typically conducted in the presence of mild agitation sufficient to maintain an essentially homogeneous mixture of the reactants.

In conducting the halogenation step, neither the rate of halogen addition nor the order of addition of the reactants is critical. Preferably, the suitable halogen is added in liquid form to the other reagents. In the usual case the isomeric mixture and catalyst are mixed homogeneously before halogen addition is begun. A typical halogenation step generally requires from about 2 hours to about 12 hours.

The preferential, aliphatic halogenation of isomeric mixtures of particular interest yield unreacted mixtures comprising 2,4-isomer (structure I) and α-halogenated 3,5-isomer (structure III).

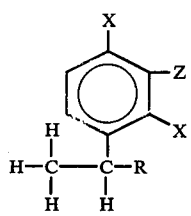

(I)

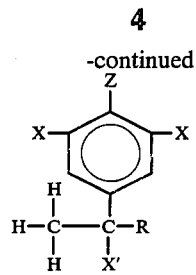

(III)

wherein X, Z and R are as above defined and X' is bromo or iodo. Compounds of the above structures are separable by distillation.

The following example is given to illustrate the invention and should not be construed as limiting its scope. All percentages in the example are by weight unless otherwise indicated.

EXAMPLE

In a 22 l. vessel equipped with a stirring means and a heating means, a mixture is formed by stirring at room temperature 6.5 l. of benzene and 3156 g. (16.7 moles) of a mixture composed of 68 percent 3,5-dichlorocumene and 32 percent 2,4-dichlorocumene. To the mixture 113 g. (0.467 mole) of benzoyl peroxide is added. The mixture is heated to 35° C and held at that temperature while halogenation with 1726 g. (10.8 moles) of bromine is conducted over a 10-hour period. The mixture is stirred and maintained at 35° C as addition of bromine creates a crude product mixture.

Then 4 l. of dichloromethane are added with stirring to the crude product mixture along with 2 l. of water in which 100 g. of sodium bisulfite is dissolved. Organic and aqueous layers are formed. The organic layer is washed first with 4 l. of 5 weight percent sodium bicarbonate and then with 5 l. of water. The benzene is removed from the organic layer under vacuum and heated to yield 3995 g. of a product mixture containing 68 percent 3,5-dichloro-α-bromocumene and 32 percent unreacted 2,4-dichlorocumene.

Similar results were achieved when the foregoing example was carried out using the free radical generators of t-butyl perbenzoate or azobisisobutyrlnitrile.

What is claimed is:

1. A process for the preferential, aliphatic bromination of a compound of structure (II) in an isomeric mixture of a compound of structure (I) and the compound of structure (II)

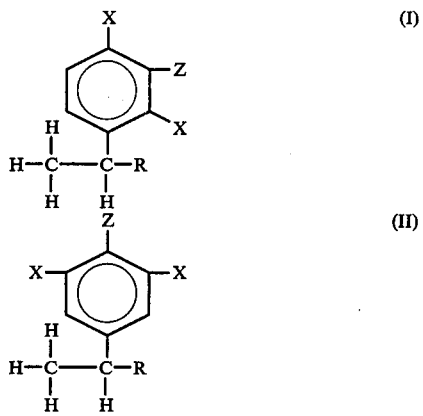

wherein each X is individually methyl, chloro, bromo, fluoro, —CF$_3$ or —CCL$_3$; Z is methyl, chloro, bromo, fluoro, —CF$_3$, —CCL$_3$, ethyl or hydrogen; R is an alkyl group containing from about 1 to about 6 carbon atoms, said process comprising the step of contacting the mixture with a brominating agent in the presence of an amount of a free radical generator and under conditions sufficient to cause bromination of the compound of structure (II) in the alpha position of the 1-sec-alkyl group whereby essentially none of the compound of structure (I) is brominated.

2. The process of claim 1 wherein the free radical generator is a peroxide.

3. The process of claim 1 wherein the brominating agent with which the mixture is contacted is gaseous bromine.

4. The process of claim 1 wherein R is methyl.

5. The process of claim 1 wherein Z is methyl or ethyl, and X is chlorine.

6. The process of claim 1 conducted at a temperature of between about 15° C and about 65° C.

7. The process of claim 1 wherein X is chlorine, Z is hydrogen, R is methyl, the free radical generator is benzoyl peroxide present in an amount between about 2.5 percent and about 4.0 percent based upon the weight of the isomeric mixture conducted at a temperature of between about 30° C and 45° C.

8. The process of claim 1 further comprising a step of separating the brominated compound of structure (II) from the resulting mixture of the brominated compound of structure (II) and the compound of structure (I).

9. A process for preferential, aliphatic bromination or iodination of a 3-substituted-1-(sec-alkyl)benzene in an isomeric mixture of (1) a 3-substituted-1-(sec-alkyl)benzene isomer having a substituent in at least the 3-ring position and optionally having substituents in the 4- and 5-ring positions and (2) a 2-substituted-1-(sec-alkyl)benzene isomer having a substituent in at least the 2-ring position and optionally having substituents in the 3- and 4-ring positions, said process comprising the step of contacting the mixture with a suitable brominating or iodinating agent in the presence of an amount of a free radical generator and under conditions sufficient to cause bromination or iodination of the 3-isomer in the alpha position of the 1-sec-alkyl group whereby essentially none of the 2-isomer is brominated or iodinated.

* * * * *